United States Patent [19]

Sauer et al.

[11] Patent Number: 6,078,638
[45] Date of Patent: Jun. 20, 2000

[54] PIXEL GROUPING FOR FILTERING CONE BEAM DETECTOR DATA DURING 3D IMAGE RECONSTRUCTION

[75] Inventors: Frank Sauer, Princeton; Kwok Tam, Edison; Bruce Ladendorf, Plainsboro, all of N.J.

[73] Assignee: Siemens Corporate Research, Inc., Princeton, N.J.

[21] Appl. No.: 09/163,494

[22] Filed: Sep. 30, 1998

[51] Int. Cl.$^7$ .................................................. A61B 6/03
[52] U.S. Cl. ................................................. 378/4; 15/901
[58] Field of Search .............................. 378/4, 8, 15, 901

[56] References Cited

U.S. PATENT DOCUMENTS

| | | | |
|---|---|---|---|
| 5,901,195 | 5/1999 | Sauer et al. ................................... | 378/4 |
| 5,970,111 | 10/1999 | Samarasekera et al. ..................... | 378/4 |
| 6,009,142 | 12/1999 | Sauer et al. ................................. | 378/15 |

*Primary Examiner*—David V. Bruce
*Attorney, Agent, or Firm*—Lawrence C. Edelman

[57] ABSTRACT

A method and apparatus for three dimensional (3D) computerized tomographic (CT) imaging of a region-of-interest (ROI) in an object, wherein image reconstruction processing is applied to a plurality of sets of pixels of 2D image data, each set being acquired on a pixelated 2D detector. The image reconstruction processing comprises filtering each of the acquired 2D image data sets for developing a corresponding plurality of filtered 2D images; and then 3D backprojecting the filtered 2D images into a common 3D space, thereby reconstructing in the 3D space a 3D image of the ROI in the object. In the present invention the filtering step comprises dividing the pixels of each set of the acquired 2D image data sets into first and second groups, and separately filtering the image data of each group to develop for each group it's own contribution to the corresponding filtered 2D image. In accordance with one embodiment of the invention, the first group essentially comprises those pixels that contribute to a given filtered 2D image in a space-invariant manner, and the second group essentially comprises those pixels that contribute to the given filtered 2D image in a space-variant manner. In accordance with another embodiment of the invention, the first group essentially comprises a contiguous portion of the pixels of each set that are entirely internal to the boundaries of a data combination mask that is applied to each set of the acquired 2D image data, and the second group essentially comprises at least one boundary region of contiguous pixels that are on or adjacent to a data combination mask boundary.

22 Claims, 6 Drawing Sheets

PIXEL GROUPING FOR FILTERING CONE BEAM DETECTOR DATA DURING 3D IMAGE RECONSTRUCTION

BACKGROUND OF THE INVENTION

1. Field of the Invention

The invention relates generally to the filtered backprojection technique for 3D image reconstruction in a cone beam x-ray imaging system, and more specifically to the division of the acquired cone beam detector data into groups for individualized filter processing.

2. Description of the Prior Art

A filtered backprojection (FBP) cone beam image reconstruction technique is described by Kudo, H. and Saito, T., in their article entitled "Derivation and Implementation of a Cone-Beam Reconstruction Algorithm for Nonplanar Orbits", IEEE Trans.Med, Imag., MI-13 (1994) 196–211.

Briefly, the FBP technique consists of the following steps at each cone beam view (i.e., at each position of the radiation source as it scans about the object, and at which an imaging detector acquires a corresponding set of projection data):

1. Compute a 1D projection (i.e., line integral) of the measured cone beam image acquired on a detector plane 1 at each of a plurality of angles θ. This step is illustrated by FIG. 1A for a given angle $\theta_1$ of a plurality of angles θ, where the projection 2 at coordinates (r,θ) comprises the integrated values of the cone beam image 4 on detector plane 1 along a plurality of parallel lines L(r,θ) that are normal to angle θ, each line L being at an incremental distance r from an origin O.

Generally, if the detector plane 1 comprises an N by N array of pixels, then the number of angles θ is typically given by $\pi N/2$.

2. Filter each 1D projection in accordance with a d/dr filter, resulting in a new set of values at each of the r,θ coordinates, such as shown by filtered projection 6 for the angle $\theta_1$ in FIG. 1A.

3. Normalize the filtered projections with a normalization function M(r,θ). Normalization is needed to take into account the number of times the plane of integration Q(r,θ) which intersects the source position and the line L(r,θ), intersects the scan path, since the data developed at each scan path intersection creates a contribution to the image reconstruction on the plane Q(r,θ).

4. Backproject the filtered projection 6 from each angle θ into a 2D object space 7 which coincides with the detector plane 1. This step is illustrated by FIG. 1B, where in lines 8 spread the value from each r,θ coordinate into 2D space 7 in a direction normal to each θ.

5. Perform a 1D d/dt filtering of the backprojection image formed in 2D space 7 by step 4. The 1D filtering is performed in the direction of the scan path, i.e., along lines 10, where the arrowhead points in the direction of the scan path.

6. Perform a weighted 3D backprojection of the resulting data in 2D space 7 (i.e., from each pixel in the detector) onto a plurality of sample points P in a 3D object volume 12. The density assigned to each point P is weighted by the inverse of the square of the distance between the point and the spatial coordinates of the x-ray source (see Equation (59) of the forenoted Kudo et al article).

The above prior art procedure will be referred to hereinafter as the 6-step process. It is assumed in this process that the entire cone beam image of the object is captured on the detector of the imaging system. Consider a plane Q(r,θ), which intersects the object, formed by the source and the line L(r,θ) on the detector at angle θ and at a distance r from the origin. Ignoring the function M(r,θ), the operations 1 through 6 compute the contribution to the reconstructed object density on the plane Q(r,θ) from the x-ray data illuminating the plane and its immediate vicinity. Since the 6-step process is detector driven, a contribution from the data illuminating the plane is computed every time the plane intersects the scan path and thus is illuminated by the x-ray beam. Consequently, the function M(r,θ) is used after the filter function in step 2 to normalize the results. Normalization is particularly undesirable since it requires pre-computing and storing a 2D array M(r,θ) for each source position along an imaging scan path. Since there are usually hundreds, if not thousands of source positions, this type of normalization is both computationally intensive and resource (computer memory) expensive.

In U.S. patent application Ser. No. 09/052,281 entitled EXACT REGION OF INTEREST CONE BEAM IMAGING USING 3D BACKPROJECTION, filed Mar. 31, 1998 and incorporated herein by reference, inventor K. Tam departs from the conventional Radon space driven conversion processing techniques for image reconstruction (such as known by his U.S. Pat. Nos. 5,257,183 and 5,453,666), and discloses a way to incorporate the technique of data combination for region-of-interest (ROI) reconstruction, with the Kudo et al. image reconstruction processing, thereby providing an image reconstruction technique for a cone beam imaging system that can not only have a spiral scan path, but can also use a short detector, In K. Tam's technique, instead of division by the function M(r,θ) as done by Kudo et al., the effect of the normalization of the reconstructed object densities is achieved by dividing the x-ray beam coverage of integration plane Q(r,θ) between the various source positions that illuminate the plane without any overlap.

K. Tam's technique comprises a 4 step process:

1) Apply a mask to the set of cone beam projection data acquired by the detector at each of the source positions, so that only specific non-overlapping contributions to the Radon data can be developed from the projection data.

2) Calculate line integral derivatives in the masked data.

3) Perform a 2D backprojection of the derivative data onto an extended height virtual detector.

4) Perform a 3D backprojection of the 2D data from the virtual detector into a 3D object space.

The presence of a detector mask ensures that the contributions developed by processing projection data of the different detectors are unique and non-redundant (FIG. 1 of this disclosure). Accordingly, division by the function M(r, θ), or its equivalent, is no longer needed; a significant simplification in the image reconstruction signal processing. However, although step 2, is not complex, it is computationally expensive. More specifically, it comprises calculating a plurality of line integrals L(r,θ) on each set of the masked detector data, to generate sampled 1D projections of the detector data. Line integral derivatives are then computed from the 1D projections by taking the difference between parallel line segments $L_1$ and $L_2$, as shown in mask 200 of FIG. 2 herein. Note that the $L_1$ and $L_2$ line segments are not limited by the boundaries of the mask, and therefore their use results in an exact calculation for the derivatives of line integrals L(r,θ). This type of masking is referred to herein as "soft masking". Additional details of such soft masking can be found in K. Tam's recently issued U.S. Pat. No. 5,748,697, incorporated herein by reference. Step 3 backprojects the line integral derivatives onto the extended "virtual" detector. Before the 3D backprojection in step 4, the gradient of the backprojected virtual detector data in the direction of the scan path is calculated, and the result is then backprojected into the 3D object space for reconstruction the ROI of the object. For good image quality, the sampling of the projections and the number of source positions needs to be very fine.

Thus, the filter process described by this U.S. Ser. No. 09/052,281 is computationally costly.

In U.S. patent application Ser. No. 09/106,537 entitled SIMPLIFIED CONE BEAM IMAGE RECONSTRUCTION USING 3D BACKPROJECTION, filed Jun. 29, 1998 and incorporated herein by reference, inventor K. Tam introduces a Feldkamp convolution processing simplification (also referred to as ramp filtering) into the above-described image reconstruction processing, wherein the entire filter process of U.S. Ser. No. 09/052,281 is replaced with a simple single step of ramp filtering of the detector data in the direction of the scan path. This simplification is illustrated in FIG. 3, where L, $L_1'$ and $L_2'$ are three closely spaced parallel line segments that are bound by a mask 300, and L is midway between $L_1'$ and $L_2'$. Line segment L is representative of many such line segments formed at various angles in mask 300, and corresponds to the previously described lines L (r,θ) of FIG. 1, which as well known to those skilled in this technology are used for computing Radon derivative data from the cone beam projection data. In the technique described in U.S. Ser. No. 09/106,537, due to the bounding of the line segments $L_1'$ and $L_2'$ by mask 300, the Feldkamp convolution processing simplification (referred to as ramp filtering) is performed as a substitute for the line integral derivative calculations, which filter processing corresponds to calculation of the Radon derivative of the partial plane defined by the line segment L and the current source position, up to a multiplicative constant.

Although this operation is computationally very fast, it yields only an approximation of the Radon derivative of the partial plane, due to errors that come about due to the "hard masking" of the endpoints of line segments $L_1'$ and $L_2'$ by mask 300, as compared to the "soft" masking shown in FIG. 2. That is, it incorrectly limits the detector pixel values to those pixels that are in the mask area, and zeros out the detector pixel values that are outside of the mask boundaries, instead of correctly limiting only the line segments L to the mask area (and calculating the line integral derivatives using the unmasked original detector data when appropriate, i.e., near the mask boundaries).

Accordingly, in U.S. patent application Ser. No. 09/123,574 filed Jul. 27, 1998 entitled MASK BOUNDARY CORRECTRION IN A CONE BEAM IMAGING SYSTEM USING SIMPLIFIED FILTERD BACKPROJECTION IMAGE RECONSTRUCTION, K. Tam describes a technique for computing 2D correction data which, when combined with the ramp filtered 2D approximation data sets, yields an exact image reconstruction. As described in greater detail in U.S. Ser. No. 09/123,574, the mathematical difference between hard and soft masking, which involves only detector data around the mask boundaries, is calculated to arrive at an additive correction term. Although this technique is mathematically correct, artifacts are still possible due to a mismatches in spatial resolution and/or position between the correction data and the ramp filtered data. Furthermore, there is no apparent way to eliminate the artifacts from this "approximation+correction" technique.

It would be desirable to provide an image reconstruction technique that has a processing speed closer to that of the forenoted U.S. Ser. No. 09/106,537, but with the image reconstruction accuracy of the forenoted U.S. Ser. No. 09/052,281.

SUMMARY OF THE INVENTION

A method and apparatus for three dimensional (3D) computerized tomographic (CT) imaging of a region-of-interest (ROI) in an object, wherein image reconstruction processing is applied to a plurality of sets of pixels of 2D image data, each set being acquired on a pixelated 2D detector at a corresponding plurality of scan path source positions. The image reconstruction processing comprises filtering each of the acquired 2D image data sets for developing a corresponding plurality of filtered 2D images, and then 3D backprojecting the filtered 2D images into a common 3D space, thereby reconstructing in the 3D space a 3D image of the ROI in the object. In accordance with the invention, a first portion of the filtering step comprises dividing the pixels of each set of the acquired 2D image data sets into first and second groups of pixels, and separately filtering the image data of each group to develop for each group it's own contribution to the corresponding filtered 2D image.

In accordance with one embodiment of the invention, the first group essentially comprises those pixels that contribute to a given filtered 2D image in a space-invariant 25 manner, and the second group essentially comprises those pixels that contribute to the given filtered 2D image in a space-variant manner. A second portion of the filtering step in the first embodiment comprises applying pre-determined image filtering information to the image data of each pixel of the first and second groups, so as to develop from that image data, image contributions to the given filtered 2D image for each group. Finally, the image contributions developed by the pixels of the first and second groups are combined to develop each filtered 2D image.

In accordance with another embodiment of the invention, the first group essentially comprises a contiguous portion of the pixels of each set that are entirely internal to the boundaries of a data combination mask that is applied to each set of the acquired 2D image data, and as such have associated therewith a space-invariant pixel-spread function (XSF). The second group essentially comprises at least one boundary region of contiguous pixels that are adjacent a boundary portion of the data combination mask, and as such have associated therewith a space-variant XSF. In the further embodiment, the second portion of the filtering step comprises applying individualized image filtering information to the image data of each of the first and second groups, so as to develop from that image data, image contributions to the given filtered 2D image for each group. Finally, the image contributions developed by the pixels of the first and second groups are combined to develop each filtered 2D image.

DETAILED DESCRIPTION OF THE INVENTION

Figure 4:
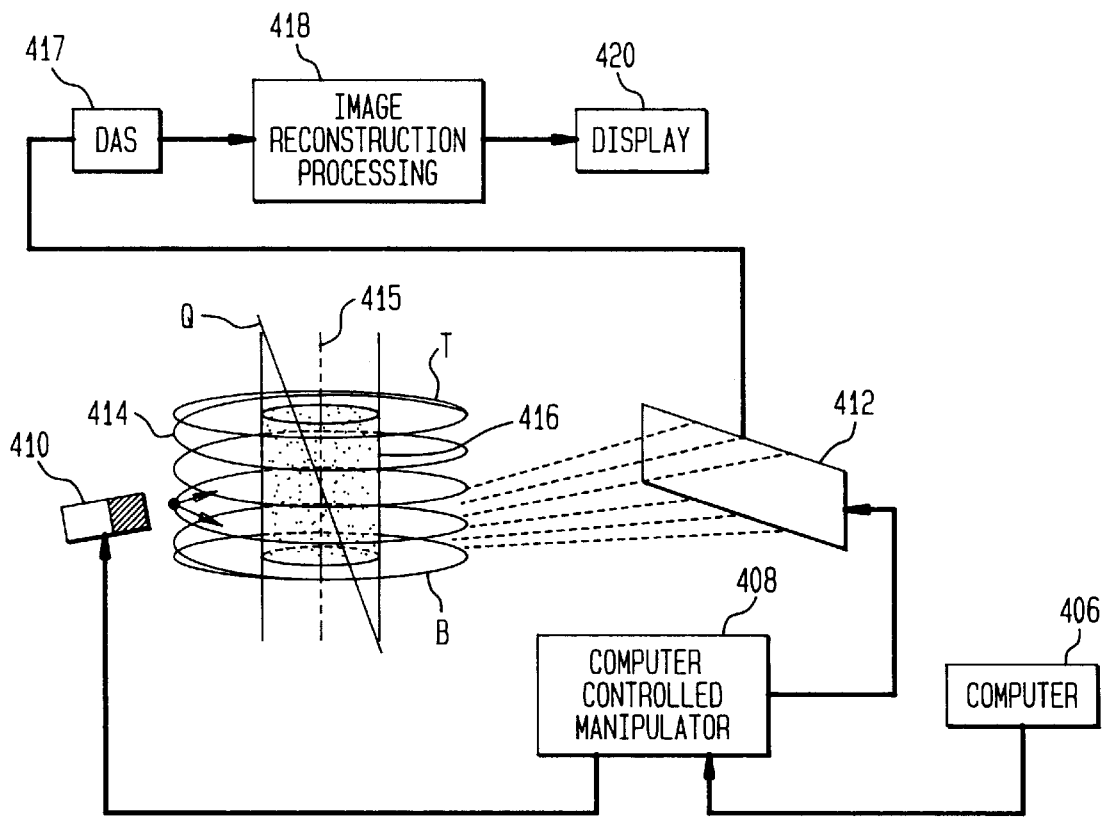
FIG. 4 illustrates a cone beam imaging apparatus useful for performing image reconstruction in accordance with the principles of the invention.

FIG. 4 illustrates a cone beam 3D CT imaging apparatus useful for acquiring and processing acquired projection data in accordance with the principles of the present invention. The illustrated imaging apparatus is constructed and operates in accordance with the same principles described in U.S. Pat. No. 5,257,183 issued Oct. 26, 1993, and U.S. Pat. No. 5,453,666 issued Oct. 31, 1995, and more specifically in accordance with the description in the forenoted U.S. Ser. No. 09/106,537, except as to be specifically described later with respect to implementation of image reconstruction processing in accordance with the present invention.

As shown in FIG. 4, in response to control signals from an appropriately programmed computer 406, a computer controlled manipulator 408 causes a source 410 of a cone or pyramid shaped beam of energy (such as x-rays) and a two-dimensional pixelated detector array 412 to cooperate (scan) at a plurality of discreet, sequentially occurring, adjacent source positions along a pre-defined source scanning path. In the illustrated embodiment the scanning path is shown as a spiral scan path 414 centered on a predetermined axis 415 of an object 416. Other types of scan paths that encircle and traverse object 416 can also be used, however, as will become apparent later, a scan path 414 exhibiting a high degree of symmetry in its parallel projection is preferred.

The only height requirement on the detector is that it should be more than the distance between adjacent turns of a projection of the spiral scan path on the detector. If only a region of interest (ROI) in object 416 is to be imaged, in a preferred embodiment, the known technique of providing a top circle scan T at the top level of the ROI and a bottom circle scan B at the bottom level of the ROI, are added.

As a result of the source/detector cooperation under control of computer 406 and manipulator 408, at each of the source positions along path 414, x-ray energy passes through the field of view of the imaging apparatus, is attenuated by object 416, and a set of projection data corresponding to the sensed x-ray energy falling on the elements (pixels) within detector 412 is developed. Each set of projection data is supplied to a data acquisition system (DAS) 417 which, like the previously described portions of FIG. 4, may operate in a fashion well known to those of ordinary skill in this technology for digitizing and storing of the acquired projection data.

In the above-noted U.S. Pat. No. 5,257,183 and 5,453,666, image reconstruction processing 418 is provided by Radon space driven conversions, thereby developing an image reconstruction of object 416 on a display 420. The present invention uses the technique of data combination for ROI reconstruction, such as described in detail in the forenoted U.S. Ser. No. 09/106,537, thereby providing a cone beam imaging system that can not only have a spiral scan path, but can also use a short detector. Instead of division by the normalization function $M(r,\theta)$ as done by Kudo et al., in the present technique normalization of the reconstructed object densities is achieved by dividing the x-ray beam coverage of plane $Q(r,\theta)$ between the various source positions that illuminate the plane without any overlap.

Figure 5:
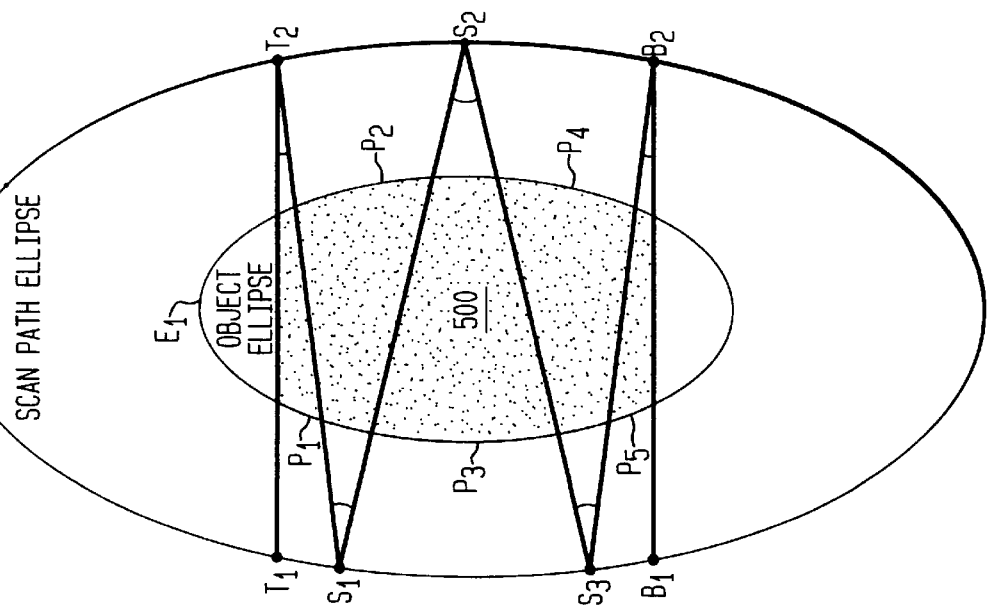
FIG. 5 illustrates a procedure for image data combination useful for understanding image reconstruction in accordance with the present invention.

More specifically, this concept of the division of x-ray beam coverage is illustrated in FIG. 5, which represents a typical integration plane $Q(r,\theta)$, such as the edge view of plane Q illustrated in FIG. 4. Since a non-vertical plane will intersect a cylinder in an ellipse, plane Q intersects object 416 and the cylindrical spiral scan path 414 in two ellipses, one inside the other, i.e., a smaller ellipse E1 and a larger ellipse E2, as shown in FIG. 5. Since spiral path 414 lies on the scan path cylinder, it intersects the plane Q in points that lie on the ellipse E2. These source positions are shown as S1, S2, and S3 in the FIG. 5. Similarly, it is easy to see that the top scan path circle intersects the plane in two points T1 and T2 which lie at the intersection between E2 and the top edge of the object's region-of-interest (shaded portion of object 216), and that the bottom circle intersects the plane in the two points B1 and B2 which lie at the intersection between E2 and the bottom edge of the object's region-of-interest. Other integration planes may have more or less spiral scan path intersections, depending upon their orientation, and may not intersect either of the top or the bottom circle scan paths.

As is apparent from FIG. 5, the source positions which illuminate that portion of integration plane Q that lies within the ROI (shaded area 500), are $T_2$, $S_1$, $S_2$, $S_3$, and $B_2$. Complete X-ray coverage of region-of-interest 500 of this portion of the integration plane can be achieved by suitably combining the data acquired at these 5 source positions, as indicated in FIG. 5. For example, at $T_2$ we only use the cone beam data within the angle bound by $T_1T_2$ and $S_1T_2$, and at $S_1$ we only use the cone beam data within the angle bound by $T_2S_1$ and $S_2S_1$. And so on. Five partial planes P1 through P5 are therefore defined by the source positions $T_2$, $S_1$, $S_2$, $S_3$, and $B_2$, which do not overlap and together completely cover the portion of plane Q that lies within ROI 500. In this way the totality of the cone beam data from each of the contributing source positions illuminates the entire plane $Q(r,\theta)$ only once without any overlap. Further details of this data combination technique can be found in K. Tam's earlier cone beam patents, such as the forenoted U.S. Ser. No. 09/106,537.

Figure 1A:
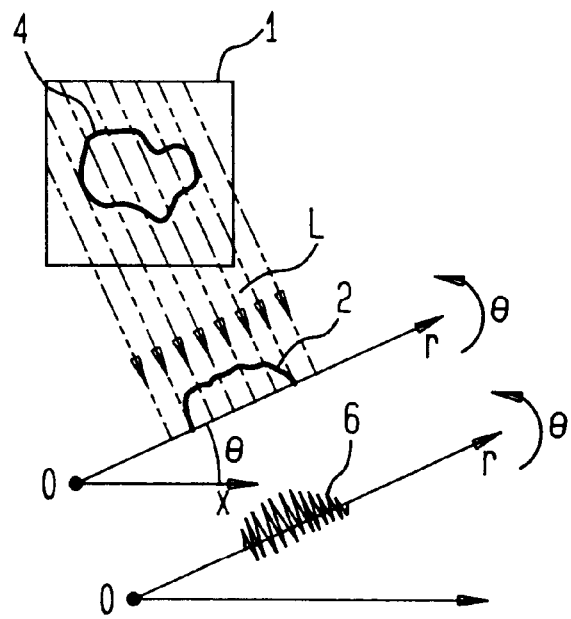
FIGS. 1A and 1B illustrate the Kudo et al. prior art 3D backprojection approach for cone beam image reconstruction, previously described.
Figure 1B:
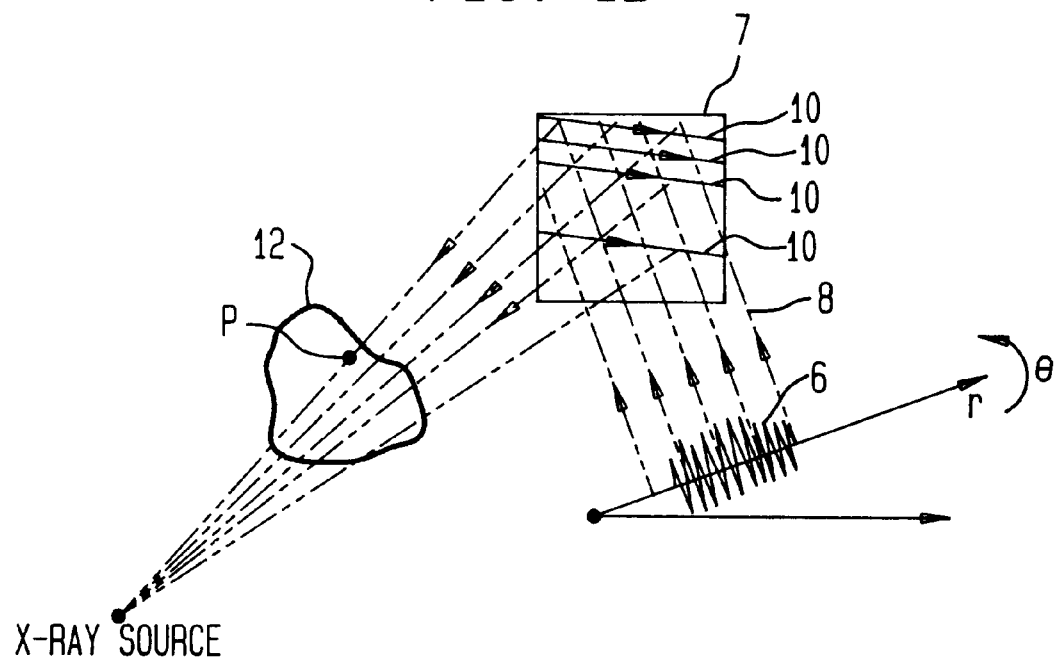
Figure 2:
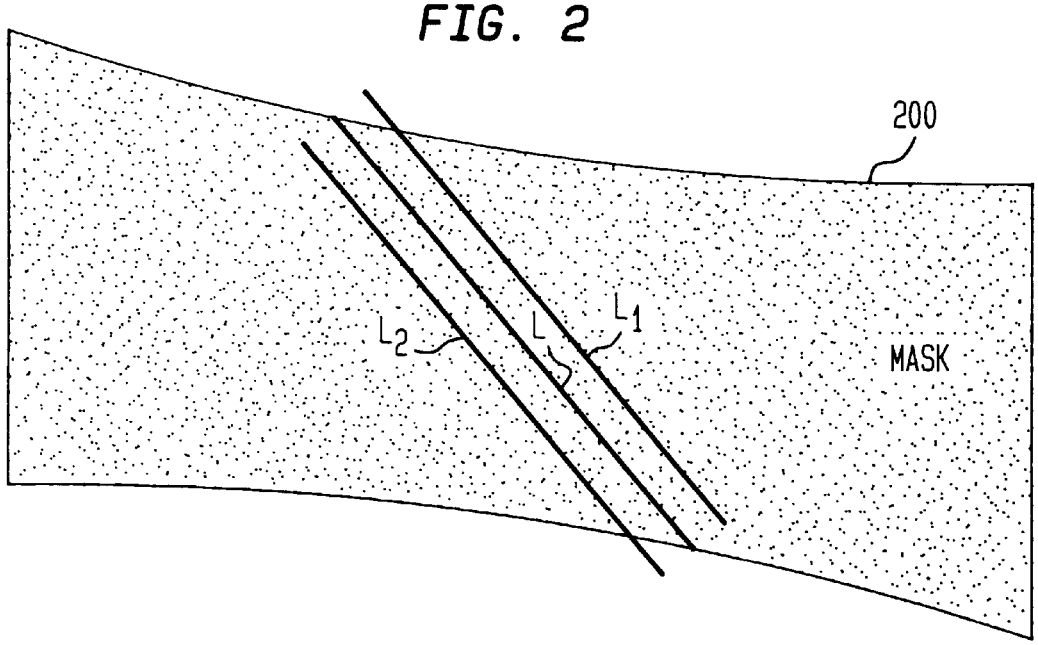
FIGS. 2 and 3 illustrate the use of data combination masks for applying soft and hard masking, respectively, to acquired 2D image.
Figure 3:
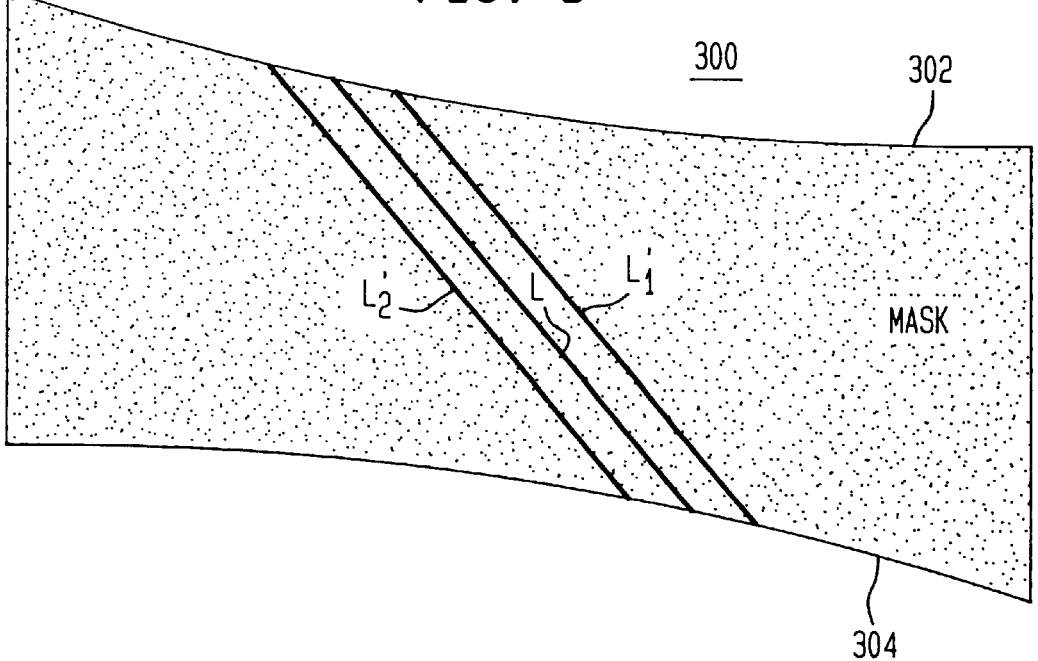

As described above, the acquired cone beam projection data should be restricted to the appropriate angular range to avoid data redundancy, and thereby avoid the need for Kudo et al's normalization function $M(r,\theta)$. For image reconstruction in accordance with the present invention, this is accomplished using a masking process. In general, the masking of acquired cone beam projection data is well known, for example see K. Tam's earlier U.S. Pat. No. 5,504,792 issued Apr. 2, 1996, as well as the forenoted U.S. Ser. No. 09/106, 537. Previously described FIG. 3 illustrates one such mask 300. Mask 300 consists of a top curve 302 and a bottom curve 304, each curve being formed by cone beam projections of the spiral scan path turn above and the spiral scan path turn below the current source position, onto the detector (412 of FIG. 4). For a flat detector located at the rotation axis such that a line connecting the source to the detector origin is normal to the detector plane, the equation for top curve 302 for the spiral scan path projection is given by:

$$y = \frac{h}{2\pi}\tan^{-1}\left(\frac{a}{x}\right)\left(1 + \frac{x^2}{a^2}\right) \quad \text{for } x \geq 0 \quad (1)$$

$$y = \frac{h}{2\pi}\left[\pi + \tan^{-1}\left(\frac{a}{x}\right)\right]\left(1 + \frac{x^2}{a^2}\right) \quad \text{for } x < 0$$

where x and y are the Cartesian coordinate axes of the detector, with the y axis coinciding with the rotation axis, a is the radius of the spiral, and h is the distance between adjacent spiral turns (the pitch). Bottom curve 304 is a reflection of top curve 302 about the origin, i.e., (x, y)→(-x, -y).

Figure 7:
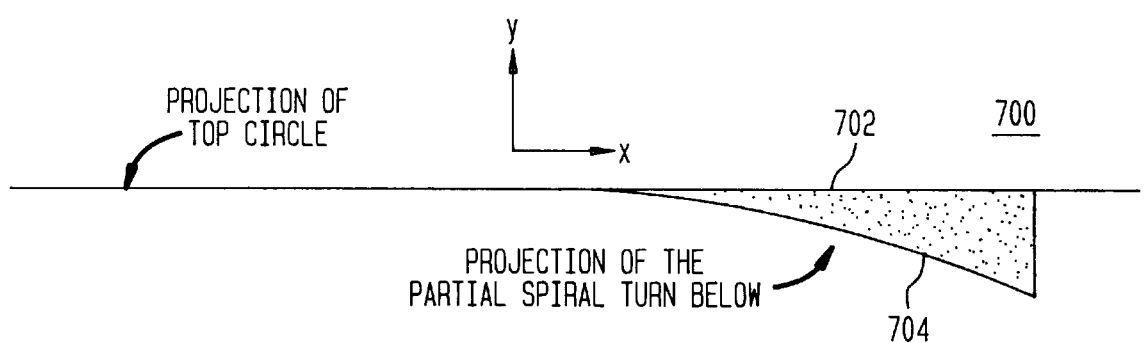
FIGS. 7 and 8 illustrate the shape of the data combination masks that are used source positions near the top and bottom of the spiral scan path shown in FIG. 2.
Figure 6:
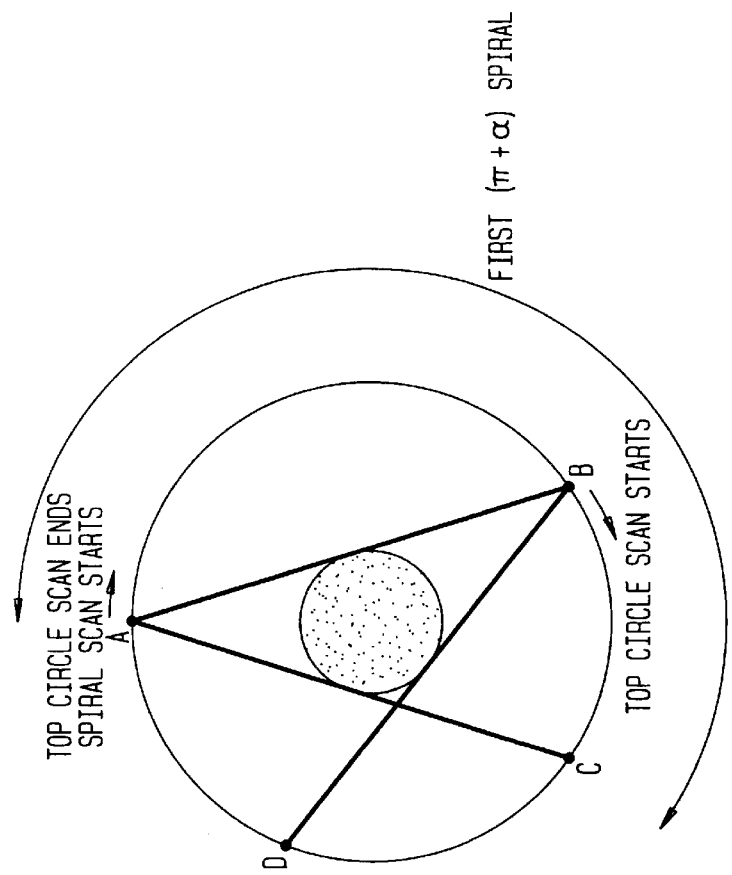
FIG. 6 is useful for understanding the generation of the data combination asks shown in FIGS. 2, 3 and 7, 8.
Figure 8:
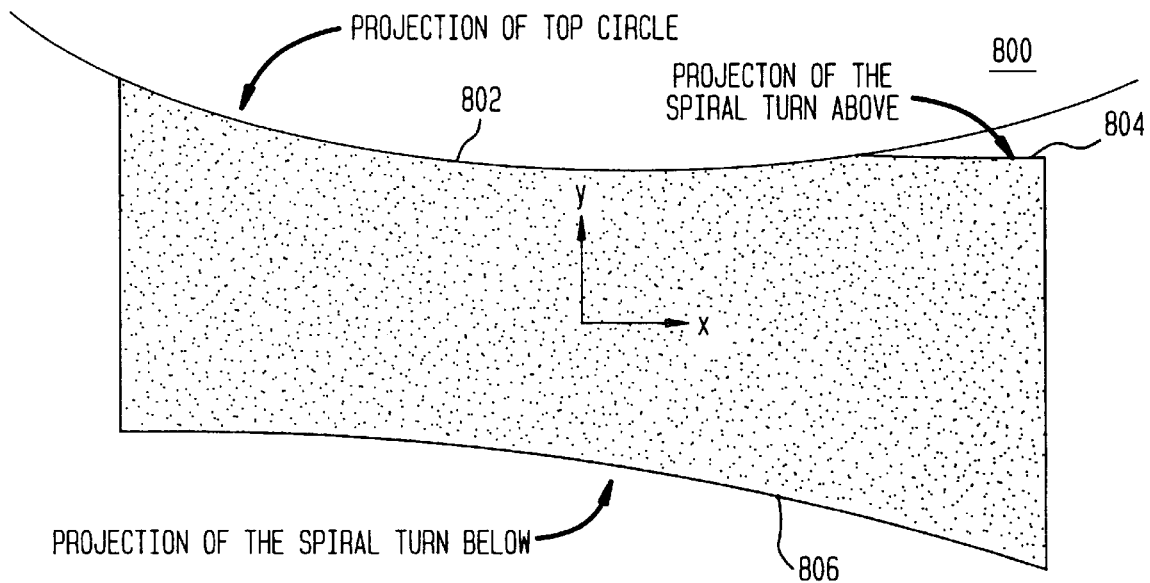

As described in conjunction with FIG. 4, for ROI imaging, circular arc scans are needed at the top and bottom levels. The top circle scan T starts at the angle (π+α) before the start of the spiral scan, and the bottom circle scan B ends at the angle (π+α) after the end of the spiral scan, where a is the fan angle of the x-ray beam. The detailed geometry of the mask used at each source position depends on the location of the source in the scan path. Accordingly, one can divide the spiral scan path into 5 distinct regions, as illustrated in FIG. 6. The first region comprises the last (π+α) turn of the top circle (clockwise from B to A). The second region comprises the first (π+α) turn of the spiral (clockwise from A to C). The third region comprises the interior portion of the spiral, i.e. after the first (π+α) turn and before the last (π+α) turn. The fourth region comprises the last (π+α) turn of the spiral (similar to the second region). The fifth region comprises the first (π+α) turn of the bottom circle (similar to the first region, but at the bottom). The masks for these 5 regions are described in greater detailed below, and are illustrated in FIGS. 7–8. These Figures assume the radiation source rotates in a spiral path from top to bottom in a clockwise direction.

(1) For the last (π+α) turn of the top circle, see mask 700 of FIG. 7, wherein:

The top curve is a horizontal line 702 at the level of the top circular arc; and The bottom curve 704 is a reflection of Equation (1) about the origin.

(2) For the first (π+α) turn of the spiral, see mask 800 of FIG. 8, wherein:

The top curve is the intersection of two curves, 802 and 804: the standard top spiral mask for Equation (1), and the cone beam projection of the top circle projected from the source given by the equation:

$$y = b\left(1 + \frac{x^2}{a^2}\right),$$

where 2b is the distance between the top and bottom circles; and

The bottom curve 806 is a reflection of Equation (1) about the origin.

(3) For the interior portion of the spiral, see mask 300 of FIG. 3, wherein:

The top curve described by Equation (1); and

The bottom curve is a reflection of Equation (1) about the origin.

For the last (π+α) turn of the spiral, see mask 800 of FIG. 8, but rotated by 1800.

For the first (π+α) turn of the bottom circle, see mask 700 of FIG. 7, but rotated by 1800.

Computer 406 of FIG. 4 can compute the masks "on-the-fly", as needed as described below during image reconstruction, or they could be pre-calculated and stored in system memory.

By appropriate use of the knowledge of data masking for image data combination, image reconstruction processing performed by processor 418 of FIG. 4 comprises filtering each of the plurality of the 2D image data sets acquired on the pixelated 2D detector 412 for developing a corresponding plurality of filtered 2D images, and then 3D backprojecting the filtered 2D images into a common 3D space, thereby reconstructing in the 3D space a 3D image of the ROI in the object.

In the present invention a first portion of the filtering step comprises dividing the pixels of each set of the acquired 2D image data sets into first and second groups, and separately filtering the image data of each group to develop for each group it's own contribution to the corresponding filtered 2D image.

In accordance with one embodiment of the invention, the first group essentially comprises those pixels that contribute to a given filtered 2D image in a space-invariant manner, and the second group essentially comprises those pixels that contribute to the given filtered 2D image in a space-variant manner. (Note, the term essentially is used to acknowledge the fact that one can purposefully make mis-assignments of few pixels into the first and second groups, without suffering significant degradation in the image reconstruction.) In this embodiment, the second portion of the filtering step comprises applying pre-determined image filtering information, in the form of pixel-spread functions (XSF's) to the image data of each pixel of the first and second groups, so as to develop from that image data, image contributions to the given filtered 2D image for each group. Finally, the image contributions developed by the pixels of the first and second groups are combined to develop each filtered 2D image.

In accordance with another embodiment of the invention, the first group comprises a contiguous portion of the pixels of each set that are entirely internal to the boundaries of a data combination mask, such as one of the masks of FIGS. 4 and 7–8, which is applied to each set of the acquired 2D image data, and the second group essentially comprises at least one boundary region of contiguous pixels with these pixels being either intersected by a data combination mask boundary or are close to one. In the further embodiment, the second portion of the filtering step comprises applying individualized image filtering information to the image data of each of the first and second groups, so as to develop from that image data, image contributions to the given filtered 2D image for each group.

The first embodiment of the invention results from the realization upon implementation of the concept of masking for image data combination, that there is a group of interior pixels of a given set of acquired 2D image data that share a single, space-invariant XSF, and are not influenced by the mask boundary. Knowledge of the XSF for a particular pixel allows one to calculate the contribution of this pixel to the filtered 2D image in an efficient way. The XSF determines how the pixel is "spread out" or distributed by the filtering process. Simple multiplication of the XSF with the scalar value of the pixel yields the contribution of the pixel to the filtered image. Accordingly, if a group of pixels share the same XSF, their contribution can be calculated as a convolution, with the XSF as the convolution kernel. A convolution can very efficiently be performed in Fourier space: the convolution of two functions in object (i.e., detector) space corresponds to the scalar multiplication of their Fourier transforms. Hence, one would transform the "subimage" consisting of the first group of pixels (all other pixel values set to zero) with a Fourier transform, multiply the result with the Fourier transform of the convolution kernel, and then apply the inverse Fourier transform to arrive at the desired filtered 2D image of the first group of pixels. This procedure is significantly faster then the straightforward multiplication of each pixel with a XSF. Accordingly, the pixels are processed "in bulk", so-to-speak, whereby the implementation of the Fourier transform as a Fast Fourier Transform is standard and very fast.

For further understanding of the application of the XSF concept as applied in the present invention, consider a linear system. One can decompose an input into a linear combination of "unit" inputs. If one knows how the unit inputs are transformed by the system, one can calculate the output as the corresponding linear combination (same coefficients) of these "unit-response functions". This concept is known, for example, in optics field. In optics, the unit input is a point, and the transformed point (image of the point) is called point-spread function. If the point-spread function is space-invariant (i.e. the same for all input point locations), the output can be written as a simple convolution of input and response function.

Since the exact reconstruction algorithm described in U.S. Ser. No. 09/052,281 is a linear algorithm, consisting of a linear filter step and a linear 3D backprojection step, the present invention introduces the concept of a pixel-spread function for the implementation of the linear filter step.

In this context, a pixel is a value at a specific location within a 2D detector data set. Note that although not specifically described, those skilled in the art understand that the 2D image data sets are originally acquired as projection images on the 2D detector array, and are then appropriately pre-processed and weighted to yield the 2D data sets used as input into the filter step. The pixel-spread function may contain this information, as well as how the image data of each pixel contributes to the filtered 2D image data. In other words, the pixel-spread function describes the "image" on a virtual detector (i.e., a detector that is large enough to view the entire ROI of the object at one position), which is generated by filtering a detector data set where the image value of the pixel at the specific location is set to one, and all other pixel values are set to zero. Note that we refer to a pixel-spread and not a point-spread function because the detector data originate as a set of data sampled by finite sized detector elements, not by mathematical points.

Figure 9:
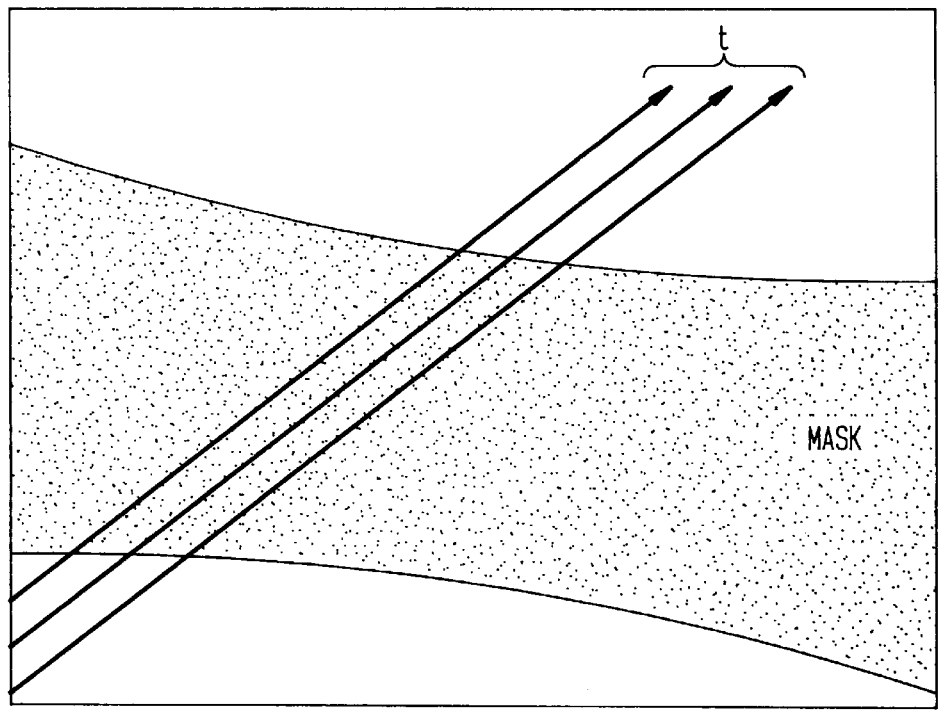
FIG. 9 illustrates ramp filtering of a masked data set.

Referring again to the first embodiment of the invention, it is noted that the space-invariant XSF for the internal pixels is mathematically equivalent to a single step of convolution processing, such as the 1D ramp filter approximation described in U.S. Ser. No. 09/106,537. Briefly, this ramp-filter like approximation is shown in FIG. 9, wherein each set of the acquired 2D projection data is masked with an appropriate mask. The masked 2D projection data are then Feldkamp ramp filtered along a plurality of parallel lines (t) formed therein, which lines are parallel with and in the direction of a parallel projection into the 2D projection data set of a line that is tangent to the scan path at the source position that acquired that 2D projection data set and in the direction of the next source position. Ramp filtering of each masked 2D projection data set along lines (t) generates a corresponding plurality of filtered 2D data sets, where the data at each point along each line represents a summation of the Radon data at that point, as would have been developed by steps 1 through 5 of the Kudo et al 6-step process. Accordingly, the only step left to reconstruct the image is 3D backprojection, corresponding to Kudo et al's step 6. This 3D backprojection step can also be accomplished by computer 406, with the resultant image reconstruction appearing on display 420. The single step of Feldkamp ramp filtering for the pixels of the first group is much faster than using the Kudo et al prior art steps 1–5, and, contrary to its use as described in the forenoted U.S. Ser. No. 09/106,537, there is no tradeoff, or price to pay for this increase in speed. More specifically, since the ramp filtering is performed on image pixel data that resides totally within the boundaries of each masked set of 2D projection data, i.e., the forenoted "hard masking" effect is absent, the developed filtered 2D image data has no loss in accuracy. Please note that the ramp-filter like function can be either 1D or 2D, determined from an ideal ramp filter with apodization (frequency window functions in horizontal and vertical directions).

For pixels which are on (or, depending on interpolation schemes, also adjacent to) a boundary portion of the mask, the XSF is space-variant. That means that these boundary pixels have their own individual XSF's. Even though these XSF's are complex 2D functions, the power of this aspect of the invention is that these functions can be pre-calculated, resulting in a significant speed-up of the image reconstruction processing during imaging operation of the system. (Of course, also the spacer invariant XSF for the interior pixels will be pre-calculated.)

There are different levels of pre-calculation corresponding to different trade-offs between the amount of memory, which is required to store the pre-calculated XSFs, and the amount of speed-up, which can be achieved during imaging operation.

The XSFs for all pixels can be pre-calculated and stored as look-up tables. Each look-up table represents the "image" on the virtual detector, which is generated by filtering the corresponding pixel image data. The entries in the table can be understood as the weight factors, with which each "source" pixel on the detector contributes to different "destination" pixels on the virtual detector. Accordingly, during imaging operation, one needs only to perform a scalar multiplication of the appropriate tabulated weight matrix (XSF) with the actual pixel value to determine a contribution to a filtered 2D image, and accumulate the resultant contribution images on the virtual detector.

XSFs can be pre-calculated and tabulated only for a subset of "source" pixels. During imaging operation, one can generate the XSFs for the other source pixels by interpolation between the stored tables.

Each XSF table can be reduced in size by removing table entries. During imaging operation missing table entries can be reconstructed by interpolation.

XSFs can be conceived as analytic (approximate or exact) functions of the relative location of "source" pixel on the detector and "destination" pixel on the virtual detector. This requires only insignificant storage space. During imaging operation, however, one has to calculate "on-the-fly" the filtered image by evaluating each function for all the virtual detector pixels.

One can combine the table look-up approach with the function approach. This may, for example, be desirable if complete coverage of the virtual detector with the look-up tables requires too much memory space, and the "far field" of the XSF, which has smaller weights than the "near field", can be approximated simply with linear or quadratic functions without unacceptable degradation of image quality.

Combinations of the above.

Variations and Extensions

Include additional linear operations in the XSF. For example, the present reconstruction processing is formulated on a planar detector array. A practical CT scanner contains, however, in general a curved detector array (part of cylinder surface). The coordinate transformation from the cylindrical to the planar detector can be included in the XSF, further speeding-up the run-time processing of the measurement data.

Implementation Issues

When using a spiral scan path, the top and bottom mask boundaries are the same for all data sets (even though acquired at the various source positions). Furthermore, top and bottom mask boundaries exhibit mutual point symmetry. This allows one to use the XSFs predetermined for the top boundary pixels, also for the bottom boundary pixels, taking the appropriate inversion symmetry into account. Exploiting this symmetry cuts the memory space requirements for the XSF look-up tables in half The XSF concept can very efficiently be mapped onto multiprocessor hardware. As the pixels are processed independently, each single processor can simply be made responsible for a certain set of detector pixels. The filtered "images" calculated by the different processors are then accumulated on the virtual detector before final backprojection into 3D object space.

Pixel-Spread Function Calculation

A table of XSF's can be easily calculated on the basis of the image reconstruction processing described in the forenoted U.S. Ser. No. 09/106,537, both for the interior and for the boundary pixels. Accordingly, one creates a set of artificial detector data, setting the value of the "source" pixel of interest to one, and the value of all the other pixels to zero. Then, one performs the image reconstruction processing described in the forenoted U.S. Ser. No. 09/106,537. The resulting image, spread out on the virtual detector, is the desired XSF.

One may fit functions to this table to calculate analytic approximations for the XSF.

One may also directly derive analytic functions from the equations described in the forenoted U.S. Ser. No. 09/106,537.

Figure 10:
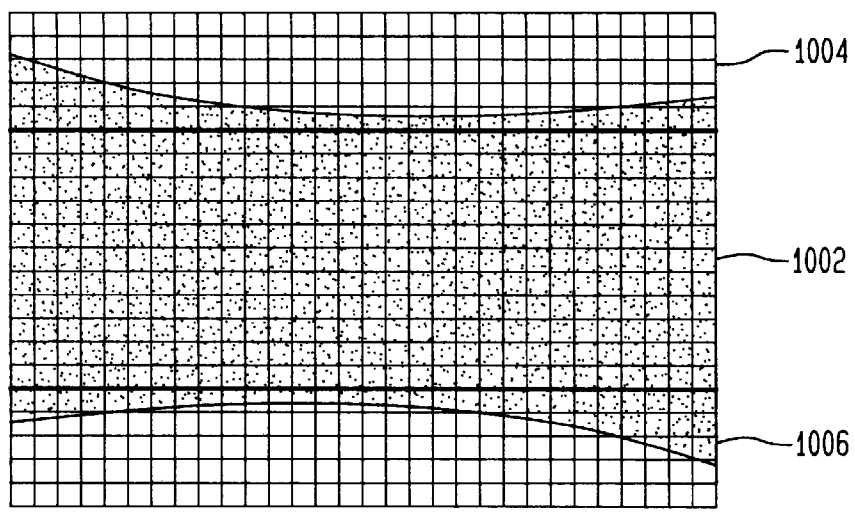
FIG. 10 illustrates another embodiment of the present invention, where a set of 2D image data having the data combination mask applied thereto is divided into three groups for individualized filter processing, each group being separated by a horizontal line.
Figure 11:
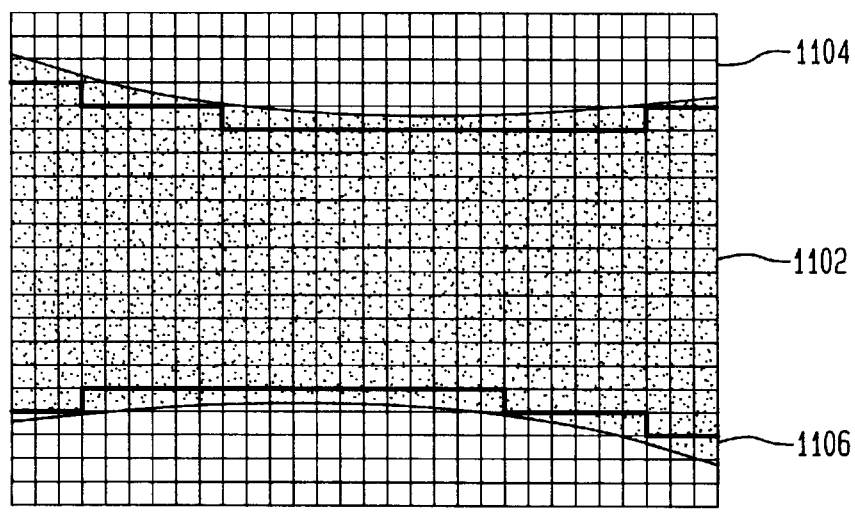
FIG. 11 illustrates an alternative embodiment to that shown in FIG. 10, for dividing the 2D image into groups using "staircase" horizontal lines.

Referring now to the second embodiment of the invention, in conjunction with an appropriate one of the data combination masks, the masked pixels of each set of acquired 2D image data are divided into regions (i.e., groups) of at least two types: a region of a first type which essentially does not contain any mask boundary pixels, and a region of a second type which essentially contains at least all of the pixels which are intersected by the mask boundary. More specifically, FIG. 10 shows a region of the first type comprising a central region 1002 of the masked 2D image data, and two outer regions 1004 and 1006, one above and below, respectively, the central region 1002, comprising the region of the second type. In FIG. 10 a shows an example where horizontal lines are used to separate these three regions, and FIG. 11 shows an example where "staircase" lines are used to separate the detector pixels into three corresponding regions 1102, 1104 and 1106.

Figure 12:
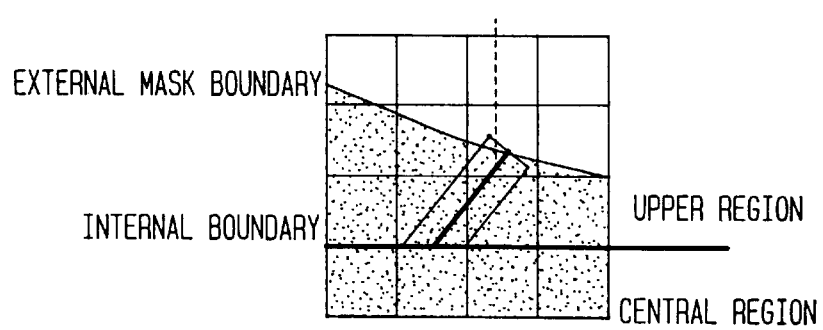
FIG. 12 illustrates how the separate groups of 2D image data having the data combination mask applied thereto, are individually processed.

In a preferred implementation of this embodiment, the central region will be filtered using a space-invariant XSF, and could be implemented as a convolution operation similar to the Feldkamp ramp filtering technique described in the forenoted U.S. Ser. No. 09/106,537. The outer regions include essentially all the pixels which need a space-variant XSF. A technique for filtering the pixel data in the outer regions is shown in FIG. 12. As shown therein, line integral derivative data, and hence filtered 2D data, is treated for the external mask boundary of the outer detector regions using the forenoted soft masking technique, and the internal boundary of the outer regions is calculated using the hard masking technique. XSF's should preferably be pre-calculated.

Variations

The detector pixel regions can be made overlapping, as long as the sum of the regions yields the original detector data. The central region can be made larger to include the boundaries or parts of the boundary. In any case, all the pixels in the central region are not influenced by the mask boundaries. Only the outer regions deal with the mask boundaries. If the central region reaches beyond the mask boundaries, the outer regions are the areas on the detector which need to be subtracted from the central region in order to yield the original masked detector.

A preferred implementation for the filtering of the outer regions is by way of look-up tables.

Thus, there has been shown and described a novel method and apparatus for image reconstruction in a cone beam CT imaging apparatus wherein the pixel data of each set of 2D projection data is grouped for individualized processing. Many changes, modifications, variations and other uses and applications of the subject invention will, however, become apparent to those skilled in the art after considering this specification and its accompanying drawings, which disclose preferred embodiments thereof Many specific examples of such variations have been given above. Additionally, it is noted that when dividing the pixels into first and second groups, it is not strictly necessary that each pixel be only in one of the groups. That is, a given pixel or group of pixels may reside in both groups, however the effect of this dual use of the pixels is taken into account when the 2D images of the first and second groups are combined. For example, one could take the XSF of a boundary pixel, which is unique, and decompose it additively into a part that is common with the interior pixels XSF (and will be taken into account by adding the pixel to the "space invariant group", possibly with a weighting factor) and individual part (that will be taken into account when the pixel is processed in the "space variant group"). All such changes, modifications, variations and other uses and applications which do not depart from the teachings herein are deemed to be covered by this patent, which is limited only by the claims which follow as interpreted in light of the foregoing description.

What is claimed is:

1. A method for three dimensional (3D) computerized topographic (CT) imaging of a region-of-interest (ROI) in an object, comprising:

acquiring a plurality of sets of pixels of 2D image data by irradiating the object with energy from a cone beam source that is directed toward a pixelated 2D detector, at a corresponding plurality of scan path source positions located about the object;

filtering each of the acquired 2D image data sets so as to develop from the pixel image data of each set a corresponding one of a plurality of filtered 2D images; and 3D backprojecting each of the filtered 2D images into a common 3D space, thereby reconstructing in said 3D space a 3D image of the ROI in the object, wherein said filtering step comprises:
- dividing the pixels of each set of the acquired 2D image data sets into first and second groups; and
- separately filtering the first and second groups of pixels so as to independently develop for each group a corresponding image contribution for a given one of the filtered 2D images.

2. The method of claim 1, wherein said filtering step comprises:
- dividing the pixels of each set of the acquired 2D image data sets into a first group comprising those pixels which contribute to the given filtered 2D image in a space-invariant manner, and into a second group comprising those pixels which contribute to the given filtered 2D image in a space-variant manner;
- applying pre-determined image filtering information to the image data of each of said first and second groups, so as to develop from each group a corresponding image contribution to the given filtered 2D image; and
- combining the image contributions developed by the pixels of said first and second groups, to develop the given filtered 2D image.

3. The method of claim 2, wherein the applying step filters all of the pixels of said first group using a common filtering operation for developing a single image contribution to the given filtered 2D image, and filters the pixels of said second group using individual filtering operations for developing a plurality of individual image contributions, which individual image contributions, when combined, develop a single image contribution as the image contribution by the second group of pixels to the given filtered 2D image.

4. The method of claim 3, wherein the applying step develops a filtered 2D image for each pixel of said second group.

5. The method of claim 2, wherein the applying step applies a common pre-determined pixel spread function as said image filtering information to the pixels of said first group, and applies a plurality of pre-determined pixel spread functions as said image filtering information to the pixels of said second group.

6. The method of claim 5, wherein the applying step operates on the image data of the pixels of said first group using a convolution operation, as an equivalent to processing with the common pre-determined pixel spread function.

7. The method of claim 5, wherein the applying step applies an individually pre-determined pixel spread function to individual ones of the pixels of said second group.

8. The method of claim 1, wherein said dividing step comprises:
- applying a data combination mask having upper and lower boundaries to each of the acquired 2D image data sets; and
- dividing the pixels of each set into a first group of pixels that essentially comprises a contiguous region of the pixels of each set that are entirely internal to the boundaries of a data combination mask that is applied to each set of the acquired 2D image data, and into a second group of pixels that essentially comprises at least one boundary region of contiguous pixels that are on or close to a data combination mask boundary.

9. The method of claim 8, wherein said separately filtering step comprises:
- applying a space-invariant pixel-spread function (XSF) filter processing to the image data of said first group, and a space-variant XSF filter processing to the image data of said second group, so as to develop from the image data of each group a corresponding image contribution to the given filtered 2D image.

10. The method of claim 8, wherein said separately filtering step comprises:
- applying a ramp filtering type processing as said space-invariant XSF to the image data of said first group, and line integral derivative processing and 2D backprojection processing as said space-variant XSF to the image data of said second group, so as to develop from the image data of each group said corresponding image contributions to the given filtered 2D image.

11. The method of claim 10, wherein said line integral derivative processing and 2D backprojection processing of the image data of said second group, develops a plurality of individual image contributions, which individual image contributions, when combined, develop a single image contribution as the image contribution by the second group of pixels to the given filtered 2D image.

12. Apparatus for three dimensional (3D) computerized tomographic (CT) imaging of a region-of-interest (ROI) in an object, comprising:
- a cone beam source for applying radiation energy to at least the ROI of the object;
- a 2D detector having a plurality of rows and columns of pixels therein for detecting radiation energy;
- means for defining a source scanning trajectory as a scan path traversed by the source;
- a manipulator for causing the cone beam source, fixed relative to the 2D detector with both source and detector movably positioned relative to the object, to scan about the ROI in the object at a plurality of source positions in a direction along the scan path, to cause the pixels of the 2D detector to acquire a set of 2D image data at each of said source positions;
- filter processing means for filtering each of the acquired 2D image data sets so as to develop therefrom a corresponding one of a plurality of filtered 2D images; and
- 3D backprojection means for 3D backprojecting each of the filtered 2D images into a common 3D space, thereby reconstructing in said 3D space a 3D image of the ROI in the object, wherein the filter processing means comprises:
- dividing means for dividing the pixels of each set of the acquired 2D image data sets into first and second groups; and
- individualized filter processing means for separately filtering the first and second groups of pixels so as to independently develop for each group a corresponding image contribution for a given one of the filtered 2D images.

13. The apparatus of claim 12, wherein:
- said dividing means causes the pixels of the first group to comprise those pixels which contribute to the given filtered 2D image in a space-invariant manner, and the second group to comprise those pixels which contribute to the given filtered 2D image in a space-variant manner; and
- said individualized filter processing means applies pre-determined image filtering information to the image data of each of said first and second groups, so as to develop from each group a corresponding image contribution to the given filtered 2D image; and then combines the image contributions developed by the pixels of said first and second groups, to develop the given filtered 2D image.

14. The apparatus of claim 13, wherein the individualized filter processing means filters all of the pixels of said first group using a common filtering operation for developing a single image contribution to the given filtered 2D image, and filters the pixels of said second group using individual filtering operations for developing a plurality of individual image contributions, which individual image contributions, when combined, develop a single image contribution as the image contribution by the second group of pixels to the given filtered 2D image.

15. The apparatus of claim 14, wherein the individualized filter processing means develops a filtered 2D image for each pixel of said second group.

16. The apparatus of claim 13, wherein the individualized filter processing means applies a common pre-determined pixel spread function as said image filtering information to the pixels of said first group, and applies a plurality of pre-determined pixel spread functions as said image filtering information to the pixels of said second group.

17. The apparatus of claim 16, wherein the individualized filter processing means includes a convolution processor for operating on the image data of the pixels of said first group using a convolution operation, as an equivalent to processing with the common pre-determined pixel spread function.

18. The apparatus of claim 16, wherein the individualized filter processing means applies an individually pre-determined pixel spread function to individual ones of the pixels of said second group.

19. The apparatus of claim 12, wherein said dividing means includes a mask generator means for applying a data combination mask having upper and lower boundaries to each of the acquired 2D image data sets, and then divides the pixels of each set into a first group of pixels that essentially comprise a contiguous region of the pixels of each set that are entirely internal to the boundaries of a data combination mask that is applied to each set of the acquired 2D image data, and into a second group of pixels that essentially comprise at least one boundary region of contiguous pixels that are on or close to a data combination mask boundary.

20. The apparatus of claim 19, wherein said individualized filter processing means includes:
 a first filter processor for applying a space-invariant pixel-spread function (XSF) filter processing to the image data of said first group, and
 a second filter processor for applying a space-variant XSF filter processing to the image data of said second group, so as to develop from the image data of each group a corresponding image contribution to the given filtered 2D image.

21. The apparatus of claim 20, wherein the first filter processor applies a ramp filtering type processing as said space-invariant XSF to the image data of said first group, and the second filter processor applies line integral derivative processing and 2D backprojection processing as said space-variant XSF to the image data of said second group, so as to develop from the image data of each group said corresponding image contributions to the given filtered 2D image.

22. The apparatus of claim 21, wherein the second filter processor develops a plurality of individual image contributions, which individual image contributions, when combined, develop a single image contribution as the image contribution by the second group of pixels to the given filtered 2D image.

* * * * *